US012691105B2

(12) United States Patent
Stuelsatz et al.

(10) Patent No.: US 12,691,105 B2
(45) Date of Patent: ***Jul. 28, 2026

(54) COMPOSITIONS CONTAINING NICOTINAMIDE AND VITAMIN B6 AND METHODS OF USING SUCH COMPOSITIONS FOR TREATING CACHEXIA OR PRECACHEXIA

(71) Applicant: SOCIETE DES PRODUITS NESTLE S.A., Vevey (CH)

(72) Inventors: Pascal Stuelsatz, Crissier (CH); Jerome Feige, Crissier (CH); Joris Michaud, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 508 days.

This patent is subject to a terminal disclaimer.

(21) Appl. No.: 18/250,887

(22) PCT Filed: Oct. 29, 2021

(86) PCT No.: PCT/EP2021/080110
§ 371 (c)(1),
(2) Date: Apr. 27, 2023

(87) PCT Pub. No.: WO2022/090457
PCT Pub. Date: May 5, 2022

(65) Prior Publication Data
US 2023/0390263 A1 Dec. 7, 2023

(30) Foreign Application Priority Data
Oct. 30, 2020 (EP) .................................... 20204859

(51) Int. Cl.
*C07D 213/67* (2006.01)
*A61K 31/4155* (2006.01)
*A61K 31/4415* (2006.01)
*A61K 31/455* (2006.01)
*A61P 21/00* (2006.01)
*C07D 213/82* (2006.01)

(52) U.S. Cl.
CPC ........ *A61K 31/4415* (2013.01); *A61K 31/455* (2013.01); *A61P 21/00* (2018.01)

(58) Field of Classification Search
CPC ................ C07D 213/67; C07D 213/82; A61K 31/4155; A61K 31/455; A61P 21/00
See application file for complete search history.

(56) References Cited

U.S. PATENT DOCUMENTS

| | | | | |
|---|---|---|---|---|
| 2012/0288588 | A1 | 11/2012 | Barron | |
| 2023/0390262 | A1* | 12/2023 | Stuelsatz | ................. A61P 21/00 |
| 2023/0390264 | A1* | 12/2023 | Stuelsatz | ................. A61P 21/00 |
| 2023/0398104 | A1* | 12/2023 | Stuelsatz | ............ A61K 31/4415 |
| 2025/0186418 | A1* | 6/2025 | Stuelsatz | ................. A61P 21/00 |

FOREIGN PATENT DOCUMENTS

| | | |
|---|---|---|
| AT | 513274 | 3/2014 |
| CN | 102688201 A | 9/2012 |
| CN | 107114800 | 9/2017 |
| CN | 109562104 A | 4/2019 |
| CN | 109588709 | 4/2019 |
| JP | H05505935 A | 9/1993 |
| JP | 2008509920 A | 4/2008 |
| WO | 2005102301 | 11/2005 |
| WO | 2013056048 | 4/2013 |
| WO | 2021004919 | 1/2021 |

OTHER PUBLICATIONS

Guo et al. "Nicotinamide protects against skeletal muscle atrophy in streptozotocin-induced diabetic mice" Archives of Physiology and Biochemistry, 2019, vol. 125, No. 5, pp. 470-477.
Suidasari et al. "Dietary vitamin B6 modulates the gene expression of myokines, Nrf2-related factors, myogenin and HSP60 in the skeletal muscle of rats" Experimental and Therapeutic Medicine, 2017, vol. 14, pp. 3239-3246.
Chinese Office Action for Appl No. 202180068552.4 dated Sep. 12, 2025, 6 pages.
Japanese Office Action for Appl No. 2023-521886 dated Feb. 17, 2026, 4 pages.

* cited by examiner

*Primary Examiner* — Brenda L Coleman
(74) *Attorney, Agent, or Firm* — K & L Gates LLP

(57) ABSTRACT

Composition containing Nicotinamide and vitamin B6 are provided. The composition may be an oral nutritional composition, for example a nutritional supplement, an oral nutritional supplement, a food product, a food for special medical purpose (FSMP). The composition can be administered to an individual in need thereof for preventing and/or treating precachexia and/or cachexia, and/or promoting muscle repair, and/or improving skeletal muscle regeneration, and/or maintaining or increasing skeletal muscle function and/or skeletal muscle mass in an individual with cachexia or precachexia.

14 Claims, 7 Drawing Sheets

A

B

A

B

A

B

A

B

A    Muscle Stem Cell amplification

B    Muscle Stem Cell commitment

A

B

Panc-1 Cell number

COMPOSITIONS CONTAINING NICOTINAMIDE AND VITAMIN B6 AND METHODS OF USING SUCH COMPOSITIONS FOR TREATING CACHEXIA OR PRECACHEXIA

CROSS REFERENCE TO RELATED APPLICATIONS

The present application is a National Stage of International Application No. PCT/EP2021/080110, filed on Oct. 29, 2021, which claims priority to European Patent Application No. 20204859.1, filed on Oct. 30, 2020, the entire contents of which are being incorporated herein by reference.

FIELD OF THE INVENTION

The present disclosure generally relates to compositions containing Nicotinamide and vitamin B6 and also relates to methods of preparing and using such compositions. The composition may be an oral nutritional composition, for example a nutritional supplement, an oral nutritional supplement, a food product, a food for special medical purpose (FSMP). The composition can be administered to an individual in need thereof for preventing and/or treating precachexia and/or cachexia, and/or promoting muscle repair, and/or improving skeletal muscle regeneration, and/or maintaining or increasing skeletal muscle function and/or skeletal muscle mass in individuals suffering from cachexia or precachexia. For example, the present invention is useful to promote muscle repair and/or regeneration in individuals suffering from precachexia or cachexia.

BACKGROUND TO THE INVENTION

Skeletal muscle regeneration is a crucial mechanism to repair and maintain muscle mass and function throughout life. Skeletal muscle regeneration primarily requires the participation of myogenic progenitors, known as muscle stem cells or satellite cells.

Non-proliferative, quiescent satellite cells, which adjoin resting skeletal muscles, can be identified by their distinct location between sarcolemma and basal lamina, a high nuclear-to-cytoplasmic volume ratio, few organelles (e.g. ribosomes, endoplasmic reticulum, mitochondria, golgi complexes), small nuclear size, and a large quantity of nuclear heterochromatin relative to myonuclei. On the other hand, activated satellite cells have an increased number of caveolae, cytoplasmic organelles, and decreased levels of heterochromatin.

These muscle satellite cells are part of the adult stem cell niche and they are involved in the normal growth of muscle, as well as regeneration following injury or disease. Hence, they are a potential target to enhance muscle regeneration in both healthy and diseased conditions. Skeletal muscle regeneration follows a series of steps that recapitulates the phases of development. Muscle progenitor cells must exit the state of quiescence and become active, proliferate and commit to myogenic differentiation.

Satellite cells express genetic markers at different stages of myogenesis and proliferation. Pax7 and Pax3 are considered to be satellite cell markers. For example, activated satellite cells expressing low levels of Pax7 are more committed to differentiation, whereas high levels of Pax7 are related to cells less prone to differentiate and have more undifferentiated stemness characteristics. Activation and the induction of myogenesis is typically regulated by myogenic regulatory factors such as MyoD, Myf5, myogenin and MRF4. Negative regulation by myostatin and TGFb inhibits the differentiation of satellite cells (Almeida et al. (2016) Muscle Satellite Cells: Exploring the Basic Biology to Rule Them, Stem Cells International, Vol. 2016, ID 1078686).

Experimental therapies which have previously included myoblast transplantation have not been entirely successful due to the reduced regenerative potential of myoblasts which are more committed and differentiated in comparison with the muscle stem cells.

Muscle stem cell function and regeneration is a potential target to enhance muscle regeneration both in healthy and diseased conditions. However, there are currently no product on the market targeting muscle stem cells, and researches for therapeutic approaches have been focused on using drugs, and are for the most part still in a preclinical stage. Nevertheless, it appears evident that the nutritional status can affect muscle stem cells and interest for nutritional interventions to target muscle stem cells has been recently growing.

Therefore, there remains a significant need to identify compounds, compositions and methods, which modulate muscle stem cells directly for maintaining muscle health and improving muscle regeneration.

SUMMARY

As set forth in the experimental examples disclosed later herein, the present inventors surprisingly identified Nicotinamide as an enhancer of both amplification and commitment of muscle stem cells and vitamin B6 as an enhancer of their commitment. The present inventors also surprisingly found that the effect of Nicotinamide and vitamin B6 when tested alone, was potentiated when cells were treated with a combination of these two compounds. This synergistic effect, that is shown and described in FIG. 3, might be explained by the fact that Nicotinamide and vitamin B6 act differently on the muscle stem cells with Nicotinamide increasing mainly the amplification step (Pax7 cells) while vitamin B6 targeting specifically the commitment step (MyoD cells). This effect has been shown specific to B6 compared with other B vitamins (e.g. B9). A composition comprising the combination was advantageous in maintaining stem cell function. In particular, a combination of Nicotinamide and vitamin B6 (e.g. pyridoxine), particularly at specific concentrations and/or specific ratios thereof, unexpectedly showed a statistically significant synergistic association between the Nicotinamide and vitamin B6 and the increase in skeletal muscle regeneration by promoting muscle stem cell function, thus suggesting an effect of these nutrients on maintaining or increasing muscle mass and/or skeletal muscle function in an individual in need thereof, especially for promoting muscle regeneration and/or muscle repair in an individual suffering from precachexia and cachexia.

In an aspect of the present disclosure, a composition comprises a combination of Nicotinamide and Vitamin B6 (e.g. pyridoxine), preferably an amount of the combination that is therapeutically effective for at least one of the physiological benefits disclosed herein.

In an embodiment, the composition comprises vitamin B6 in an amount of a daily dosage of 1.0-600 mg of vitamin B6/day, for example 1.0-200.0 mg of vitamin B6/day, for example 1.0-25.0 mg of vitamin B6/day, for example 1.0-15.0 mg of vitamin B6/day, for example 1.0-10 mg of vitamin B6/day, for example 1.0-7.0 mg of vitamin B6/day.

In an embodiment, the composition comprises Nicotinamide in an amount of a daily dosage of about 1 mg/day to about 3000 mg/day, for example about 10 mg/day to about 2000 mg/day, for example about 500 mg/day to about 1000 mg/day.

In an embodiment, the Vitamin B6 is administered in an amount of 10.0 to 20.0 mg vitamin B6 per day and/or the Nicotinamide is administered in an amount of about 500 mg to about 1000 mg Nicotinamide per day.

However, in any given case, the amount of compound administered will depend on such factors as the solubility of the active component, the formulation used, subject condition (such as weight), and/or the route of administration. For example, the daily doses of Vitamin B6 or Nicotinamide disclosed above are non-limiting and, in some embodiments, may be different; in particular, the compositions disclosed herein can be utilized as an acute care food for special medical purposes (FSMP).

In an embodiment, the composition is in a form of a solid powder, a powdered stick, a capsule or a solution. The composition can be a food supplement, a medical food, a nutritional composition, for example an oral nutritional composition.

[In another aspect of the present disclosure, a method of preparing the composition is provided. The method can comprise combining vitamin B6 and Nicotinamide, and preferably an amount of the resultant combination that is therapeutically effective for at least one of the physiological benefits disclosed herein.

In another aspect of the present disclosure, a nutritional supplement comprises a therapeutically effective amount of any of the compositions disclosed herein. In an embodiment, the nutritional supplement is an oral nutritional supplement (ONS). The nutritional supplement can be in a form of a solid powder, a powdered stick, a capsule, or a solution. In an embodiment, the nutritional supplement comprises vitamin B6 in an amount of a daily dosage of 1.0-600 mg vitamin B6, for example 1.0-200 mg vitamin B6, for example 1.0-25.0 mg vitamin B6. The nutritional supplement comprises Nicotinamide in a total daily dosage about 1 mg/day to about 3000 mg/day, preferably about 10 mg/day to about 2000 mg/day, more preferably from 500 mg/day to about 1000 mg/day.

In another aspect of the present disclosure, a food product comprises any of the compositions disclosed herein. In an embodiment, the food product is a food for special medical purpose (FSMP). The food product can comprise vitamin B6 in a daily dosage of 1.0-600 mg vitamin B6, for example 1.0-200 mg vitamin B6, for example 1.0-25.0 mg vitamin B6. The nutritional supplement comprises Nicotinamide in a total daily dosage about 1 mg/day to about 3000 mg/day, preferably about 10 mg/day to about 2000 mg/day, more preferably from 500 mg/day to about 1000 mg/day.

In an embodiment, the food product further comprises one or more additional ingredients, for example a lipid, a protein, a carbohydrate, a vitamin, a mineral, or any combination thereof.

In another aspect of the present disclosure, a kit comprises a therapeutically effective amount of any of the compositions disclosed herein. In an embodiment, the kit is configured for oral administration of the composition. For example, the kit can comprise at least two capsules in which a first capsule comprises the vitamin B6 (preferably functional vitamin B6) and a second capsule comprises Nicotinamide. In an embodiment, the kit comprises vitamin B6 in the first capsule in a daily dosage of 1.0-600 mg vitamin B6, for example 1.0-200 mg vitamin B6, for example 1.0-25.0 mg vitamin B6. In an embodiment, the kit comprises Nicotinamide or derivatives in the second capsule in a total daily dosage of about 1 mg/day to about 3000 mg/day, preferably about 10 mg/day to about 2000 mg/day, more preferably from 500 mg/day to about 1000 mg/day In another aspect of the present disclosure, a method of preventing and/or treating precachexia and/or cachexia, and/or promoting muscle repair, and/or improving skeletal muscle regeneration, and/or maintaining or increasing skeletal muscle function and/or skeletal muscle mass is provided. The method comprises administering to an individual in need thereof a therapeutically effective amount of a combination of vitamin B6 and Nicotinamide and/or derivatives. In an embodiment, the administration is by oral administration. In another embodiment, the administration is by intravenous administration.

The present invention also relates to a method for treating or preventing cachexia or precachexia comprising administering to a subject an effective amount of a composition of the invention. In one embodiment, the subject is identified as having precachexia or cachexia.

In an embodiment the cachexia or precachexia is associated with a disease selected from cancer, chronic heart failure, renal failure, chronic obstructive pulmonary disease, AIDS, autoimmune disorders, chronic inflammatory disorders, cirrhosis of the liver, anorexia, chronic pancreatitis, metabolic acidosis and/or neurodegenerative disease.

In a preferred embodiment of the invention, the cachexia is associated with cancer, otherwise referred to a cancer cachexia.

In an embodiment the invention provides a method of treatment of cancer cachexia, wherein the cachexia is associated with a cancer selected from pancreas, esophagus, stomach, bowel, bladder, lung and/or liver cancer.

In yet another embodiment of the invention, the invention provides a method of treatment of cancer cachexia wherein treatment of cancer cachexia is measured by reducing body weight loss, preventing body weight loss, maintaining body weight or increasing body weight.

In another embodiment of the invention, a compound or a composition of the invention may be used in a method of treatment wherein cancer cachexia is a result of treatment for cancer with a chemotherapeutic agent.

In a further embodiment of the invention, a compound or a composition of the invention may be used in a method of prevention or treatment of cachexia or precachexia in combination with a dietary intervention of high caloric, high protein, high carbohydrate, Vitamin B12 and/or Vitamin D supplementation, antioxidants, poly-unsaturated and omega 3 fatty acids, butyrate, and/or polyphenols.

In one embodiment, the subject is a human subject. In another embodiment, the subject is a companion animal, preferably a dog.

Human Skeletal Muscle Myoblasts were purchased from Lonza (https://bioscience.lonza.com). These cells were isolated from the upper arm or leg muscle tissue of normal donors and used after the second passage. Several donors were tested to ensure cell viability and purity before selecting the final donors, which are a 20-year-old Caucasian female (refer thereafter as Donor 1), a 36-year-old Caucasian female (refer thereafter as Donor 2) and a 18-year-old Caucasian male (refer thereafter as Donor 3). Human primary myoblasts were seeded in 384 well plates at a density of 1'000 cells per well in skeletal muscle growth medium (SKM-M, AMSbio). For treatment, compounds were directly added to the myoblast cultures 16 hours after initial plating.

Figure 1:
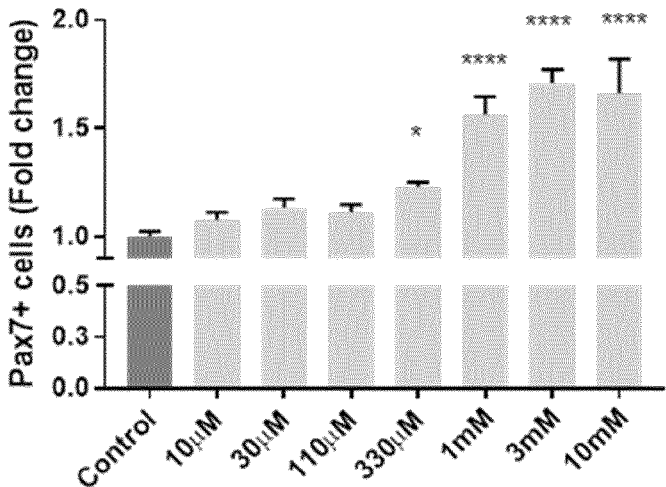
FIGS. 1 to 5—Myogenic amplification and commitment of muscle stem cells
Figure 1:
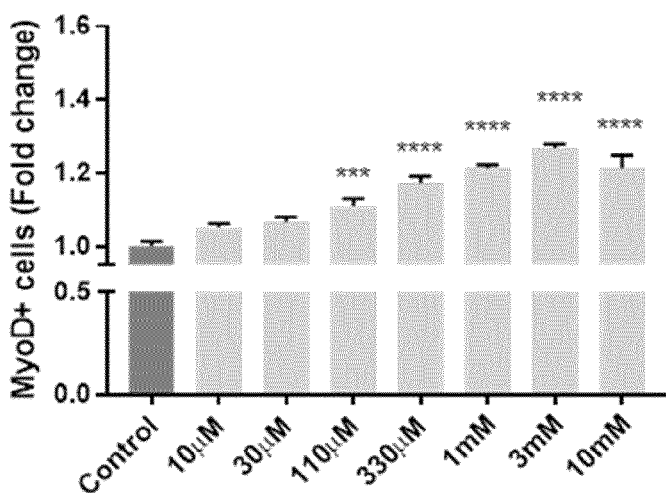
Figure 2:
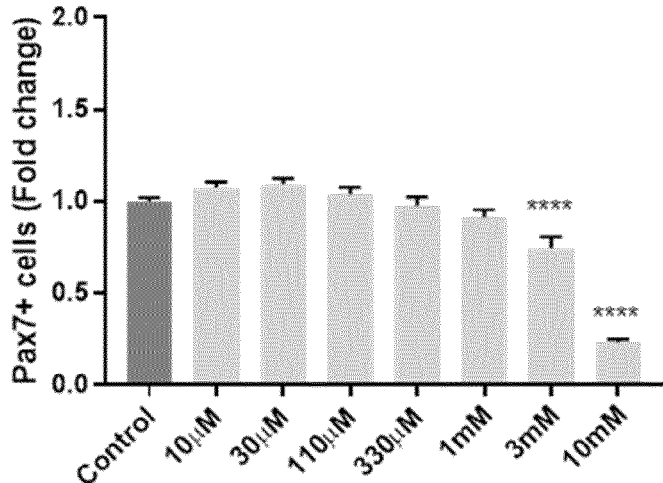
Figure 2:
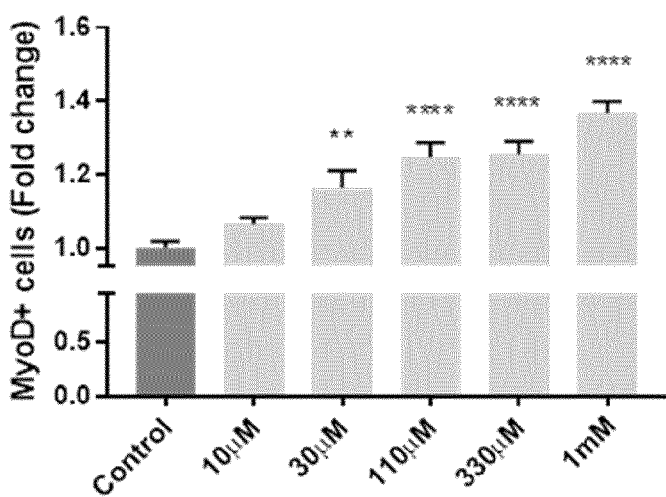
Figure 3:
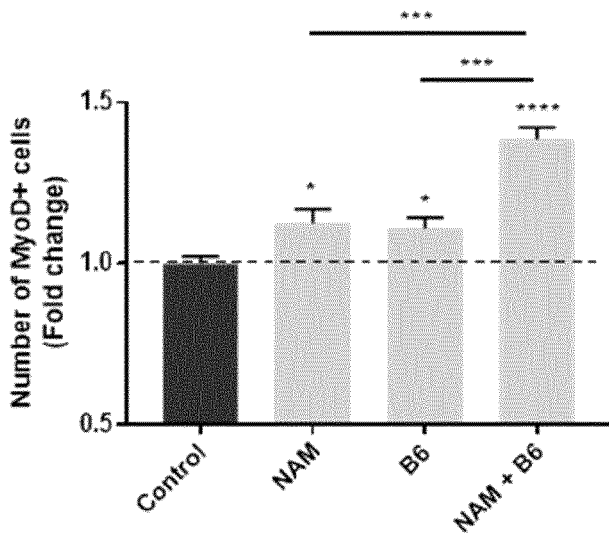
Figure 3:
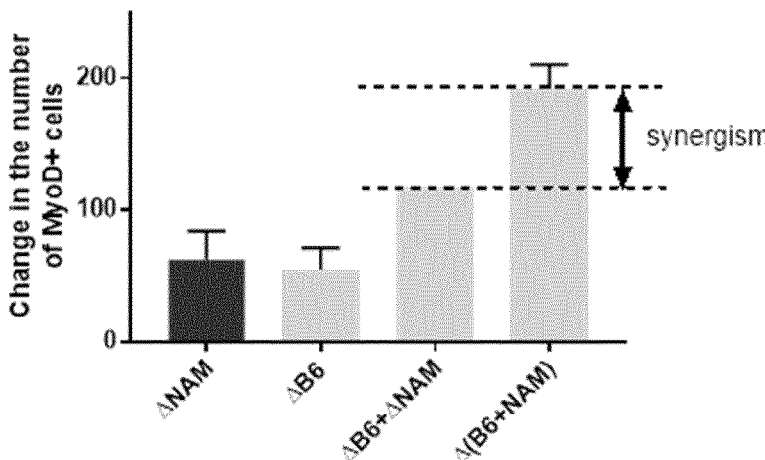

All cultures were then grown for 96 hours. Cells were stained for Pax7 and MyoD expression using antibodies directed against Pax7 and MyoD and counterstained with Hoechst 33342 to visualize cell nuclei. Pax7+ cells are defined as cells that express Pax7 regardless of MyoD expression. MyoD+ cells are defined as cells that do not express Pax7 but express MyoD. Image acquisition was performed using the ImageXpress (Molecular Devices) platform. Custom module analysis based on Multi-Wavelength Cell Scoring of the MetaXpress software was used for quantification. *, , *, ** indicates difference from the control, One-way ANOVA, with $p<0.05$, $p<0.01$, $p<0.001$, $p<0.0001$, respectively. Data are presented as Mean+/−SEM FIG. 1: In vitro dose response of Nicotinamide. Data are obtained from Human primary myoblasts from donor 4 and 8 were pooled. For each condition, the total number of cells was determined to evaluate compound toxicity, and the number of Pax7+ or MyoD+ cells was normalized to the total cell number in order to evaluate the proportion of this population and expressed as a fold change compared to the control condition (DMSO 1%). FIG. 1A represents the proportion of Pax7+ cells and FIG. 1B represents the proportion of MyoD+ cells FIG. 2: In vitro dose response of Vitamin B6. Data are obtained from Human primary myoblasts from donor 4 and 8 were pooled. For each condition, the total number of cells was determined to evaluate compound toxicity, and the number of Pax7+ or MyoD+ cells was normalized to the total cell number in order to evaluate the proportion of this population and expressed as a fold change compared to the control condition (DMSO 1%). FIG. 2A represents the proportion of Pax7+ cells and FIG. 2B represents the proportion of MyoD+ cells FIG. 3: Synergistic effect of Nicotinamide (NAM) and Vitamin B6. The effect of nicotinamide and pyridoxine alone or combined on the MyoD+ cells was assessed on Human primary myoblasts from donor 3. For each condition, the number of MyoD+ cells was normalized to the number of MyoD+ cells in the control condition (DMSO 1%). FIG. 3A represents the number of MyoD+ cells normalized to the control condition. FIG. 3B** represents the increase in MyoD+ cell number compared to the control condition (DMSO 1%). ΔB6 or NAM refers to the change from the control condition with B6 or NAM treatment, respectively. ΔB6+ANAM refers to the theoretical sum of the effects of B6 and NAM measured separately. Δ(B6+NAM) refers to the experimental effects of a combined treatment with B6 and NAM. A statistically significant synergistic effect between the nicotinamide and pyridoxine has been observed by applying a linear regression model (interaction term, p=0.05).

Figure 4:
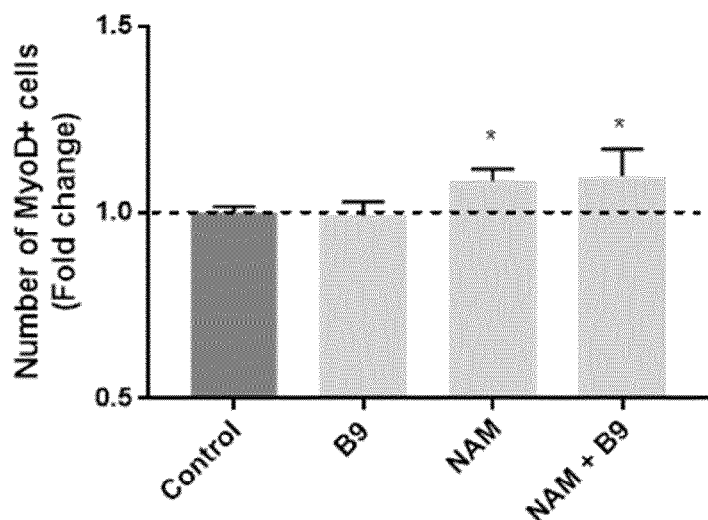
Figure 4:
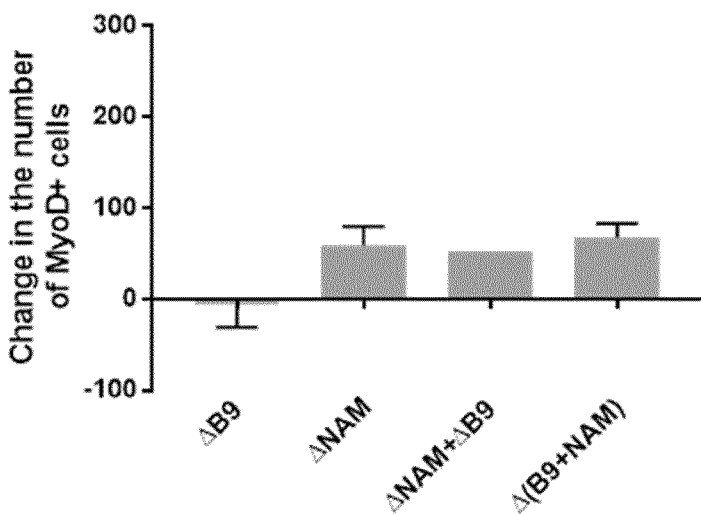

FIG. 4: Combination of Nicotinamide (NAM) with vitamin B9. The effect of nicotinamide and vitamin B9 alone or combined on the MyoD+ cells was assessed on Human primary myoblasts from donor 3. For each condition, the number of MyoD+ cells was normalized to the number of MyoD+ cells in the control condition (DMSO 1%). FIG. 4A represents the number of MyoD+ cells normalized to the control condition. FIG. 4B represents the increase in MyoD+ cell number compared to the control condition (DMSO 1%).

Figure 5:
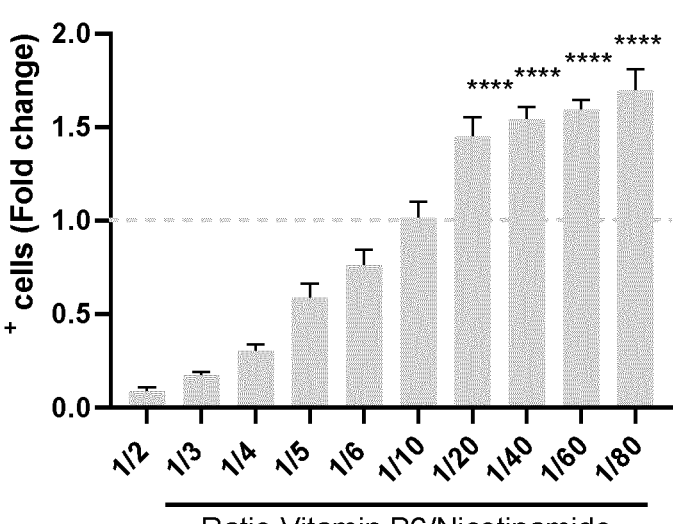

FIG. 5: represents the number of Pax7+ cells for different ratios between Pyridoxine and Nicotinamide (ratio Vitamin B6/NAM).

Figure 6:
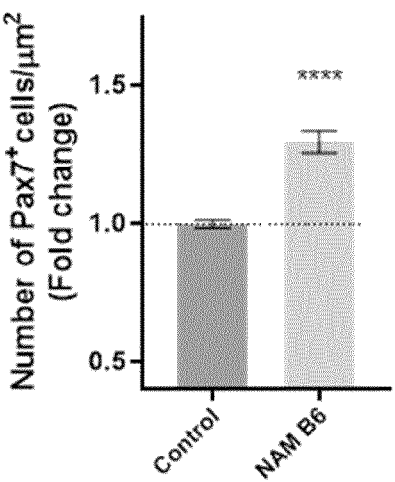
Figure 6:
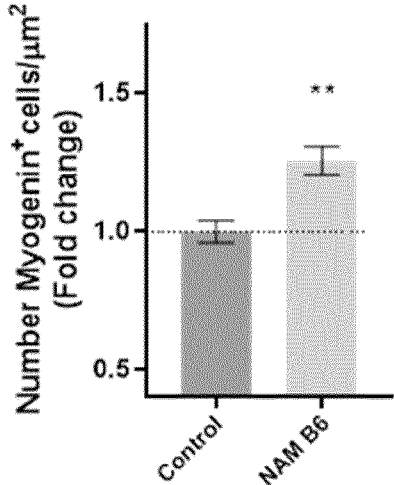

FIG. 6: In vivo effect of the combination of nicotinamide and pyridoxine on muscle stem cells function In order to reproduce the physiological process of muscle regeneration that occurs in adult skeletal muscles in response to injury or disease, we performed an intramuscular injection of cardiotoxin into mouse hindlimb muscles. One week prior to the induction of the muscle injury, mice were given by oral gavage our compounds of interest (nicotinamide and Vitamin B6 at 200 and 4 mg/kg body weight, respectively) vs. water control. Mice were treated once a day until the end of the experiment. To evaluate the efficiency of the muscle regeneration, muscles that have been previously injured were harvested 5 days after the injury and cryosections were prepared. Several myogenic markers were then measured. Cryosections were stained for Pax7, Myogenin, laminin (to delineate myofibers) and embryonic Myosin Heavy Chain (to define the injured/regenerating area) expression using specific antibodies and counterstained with Hoechst 33342 to visualize cell nuclei. Early phase of expansion and subsequent phase of myogenic differentiation of Muscle Stem Cells were evaluated by counting the number of Pax7+ cells (FIG. 6A) and Myogenin+ cells (FIG. 6B), respectively. Data are expressed as number of cells per arear of injured muscle. *, , *, **** indicates difference from the control, One-way ANOVA, with $p<0.05$, $p<0.01$, $p<0.001$, $p<0.0001$, respectively. Data are presented as Mean+/−SEM.

Figure 7:
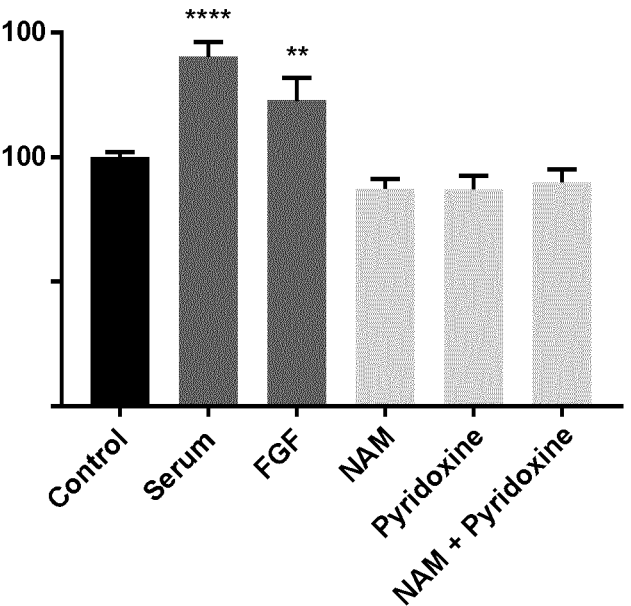
Figure 7:
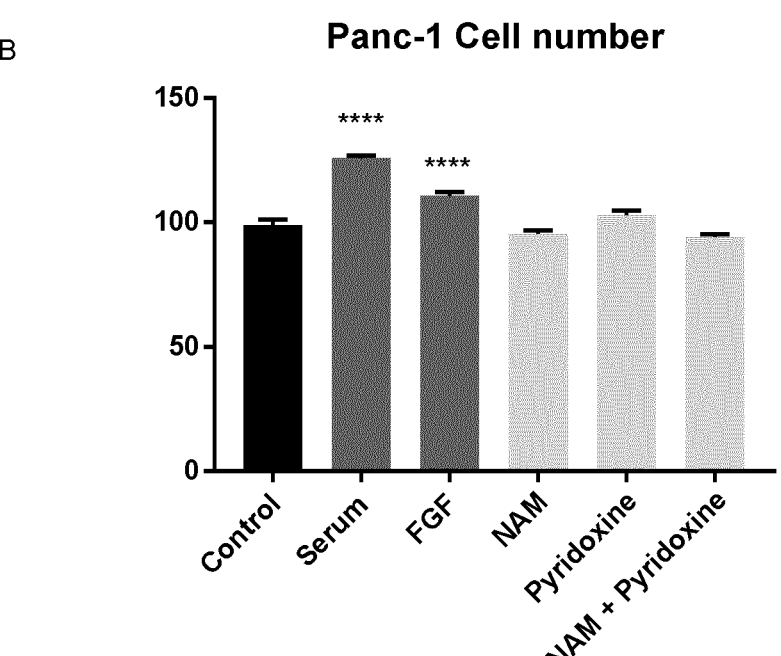

FIG. 7: Safety of compounds as non-oncogenic

The safety of the compounds was tested in two different human cancer cell lines purchased from ATCC. FIG. 7A cell line PC-3 was of prostate/adenocarcinoma from a Caucasian male, aged 62 years and FIG. 7B cell line PANC-1 was from a pancreatic duct epitheloid carcinoma from a Caucasian male, aged 56 years. Serum and FGF (Fibroblast Growth Factor) conditions were used as positive controls. *, , *, **** indicates difference from the control, One-way ANOVA, with $p<0.05$, $p<0.01$, $p<0.001$, $p<0.0001$, respectively. Data are presented as Mean+/−SEM.

DETAILED DESCRIPTION OF THE INVENTION

Definitions

Some definitions are provided hereafter. Nevertheless, definitions may be located in the "Embodiments" section below, and the above header "Definitions" does not mean that such disclosures in the "Embodiments" section are not definitions.

All percentages expressed herein are by weight of the total weight of the composition unless expressed otherwise. When reference herein is made to the pH, values correspond to pH measured at 25° C. with standard equipment.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including," "containing" and "having" should all be construed to be inclusive, unless such a construction is clearly prohibited from the context. Further in this regard, these terms specify the presence of the stated features but not preclude the presence of additional or further features.

Nevertheless, the compositions and methods disclosed herein may lack any element that is not specifically disclosed herein. Thus, a disclosure of an embodiment using the term "comprising" is (i) a disclosure of embodiments having the identified components or steps and also additional components or steps, (ii) a disclosure of embodiments "consisting essentially of" the identified components or steps, and (iii) a disclosure of embodiments "consisting of" the identified components or steps. Any embodiment disclosed herein can be combined with any other embodiment disclosed herein.

The term "and/or" used in the context of "X and/or Y" should be interpreted as "X," or "Y," or "X and Y." Similarly, "at least one of X or Y" should be interpreted as "X," or "Y," or "X and Y." For example.

Where used herein, the terms "example" and "such as," particularly when followed by a listing of terms, are merely exemplary and illustrative and should not be deemed to be exclusive or comprehensive.

A "subject" or "individual" is a mammal, preferably a human. As used herein, an "effective amount" is an amount that prevents a deficiency, treats a disease or medical condition in an individual, or, more generally, reduces symptoms, manages progression of the disease, or provides a nutritional, physiological, or medical benefit to the individual.

The terms "treatment" and "treat" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The terms "treatment" and "treat" do not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment" and "treat" are also intended to include the potentiation or otherwise enhancement of one or more primary prophylactic or therapeutic measures. As non-limiting examples, a treatment can be performed by a patient, a caregiver, a doctor, a nurse, or another healthcare professional.

A "kit" means that the components of the kit are physically associated in or with one or more containers and considered a unit for manufacture, distribution, sale, or use. Containers include, but are not limited to, bags, boxes, cartons, bottles, packages of any type or design or material, over-wrap, shrink-wrap, affixed components (e.g., stapled, adhered, or the like), or combinations thereof.

The term "food for special medical purpose (FSMP)" refers to formula foods specially processed and prepared in order to meet special needs for nutrient or diet of those suffering from food intake restriction, disorder of digestive absorption, disorder of metabolic or certain diseases. Such foods shall be used alone or together with other foods under the guidance of a doctor or clinical nutritionist. FSMP is special dietary food, not medicine, but not ordinarily eaten by normal people. It is specially developed by clinicians and nutritionists based on scientific facts after extensive medical research.

The term "oral nutritional supplement (ONS)" refers to sterile liquids, semi-solids or powders, which provide macro and micronutrients. They are widely used within the acute and community health settings for individuals who are unable to meet their nutritional requirements through oral diet alone.

As used herein, "vitamin B6" can include one or more of the following: pyridoxine (PN), pyridoxal 5'-phosphate (PLP), pyridoxine 5'-phosphate (P5P), pyridoxal (PL), pyridoxamine (PM), pyridoxamine 5'-phosphate (PMP), 4-pyridoxic acid, and pyritinol. In a preferred embodiment, at least a portion of any vitamin B6 is PN. At least a portion of the vitamin B6 can be PLP. Absorbed pyridoxamine is converted to PMP by pyridoxal kinase, which is further converted to PLP by pyridoxamine-phosphate transaminase or pyridoxine 5'-phosphate oxidase which also catalyzes the conversion of PNP to PLP.[2] Pyridoxine 5'-phosphate oxidase is dependent on flavin mononucleotide (FMN) as a cofactor produced from riboflavin (vitamin B2). In a preferred embodiment the vitamin B6 is pyridoxine.

EMBODIMENTS

An aspect of the present disclosure is a composition comprising Nicotinamide and vitamin B6. The composition comprising the Nicotinamide and vitamin B6 is advantageous in preventing and/or treating precachexia and/or cachexia, and/or promoting muscle repair, and/or improving skeletal muscle regeneration, and/or maintaining or increasing skeletal muscle function and/or skeletal muscle mass. For example, the composition comprising the Nicotinamide and vitamin B6 is useful to promote muscle repair and/or regeneration in individuals suffering from precachexia and cachexia.

Composition

Nicotinamide

Nicotinamide, also known as niacinamide or nicotinic acid amide, is the water-soluble, active form of vitamin B3.

The nicotinamide can be administered in an amount of 0.001 mg/day to about 3000 mg/day, for example about 1 mg/day to about 3000 mg/day, for example about 10 mg/day to about 2000 mg/day, for example about 500 mg/day to about 1000 mg/day. Of course, the daily dose can be administered in portions at various hours of the day. However, in any given case, the amount of compound administered will depend on such factors as the solubility of the active component, the formulation used, subject condition (such as weight), and/or the route of administration. For example, the daily doses of nicotinamide disclosed above are non-limiting and, in some embodiments, may be different; in particular, the compositions disclosed herein can be utilized as an acute care food for special medical purposes (FSMP) and contain up to about 3.0 g nicotinamide/day.

9

Pyridoxine

Pyridoxine is the 4-methanol form of vitamin B6, an important water-soluble vitamin that is naturally present in many foods.

In an embodiment, vitamin B6 can include one or more of the following: pyridoxine (PN), pyridoxal 5'-phosphate (PLP), pyridoxine 5'-phosphate (P5P), pyridoxal (PL), pyridoxamine (PM), pyridoxamine 5'-phosphate (PMP), 4-pyridoxic acid, and pyritinol. In a preferred embodiment, at least a portion of any vitamin B6 is PN. At least a portion of the vitamin B6 can be PLP. Absorbed pyridoxamine is converted to PMP by pyridoxal kinase, which is further converted to PLP by pyridoxamine-phosphate transaminase or pyridoxine 5'-phosphate oxidase which also catalyzes the conversion of PNP to PLP. Pyridoxine 5'-phosphate oxidase is dependent on flavin mononucleotide (FMN) as a cofactor produced from riboflavin (vitamin B2).

In an embodiment, Vitamin B6 can be administered in an amount of vitamin B6 in a daily dosage of about 1.0-600 mg vitamin B6, for example about 1.0-200 mg vitamin B6, for example about 1.0-25.0 mg vitamin B6, for example about 10-20 mg of Vitamin B6/day. In an embodiment, the combination is particularly effective, in particular on both amplification and commitment of muscle cells, when the vitamin B6: Nicotinamide are present in a ratio of from about 1:100 to about 1:9, preferably from about 1:80 to about 1:20, preferably from about 1:75 to about 1:25, more preferably from about 1:60 to about 1:30. In one embodiment, the pyridoxine: Nicotinamide are present in a ratio of from about 1:45 to about 1:30.

In some embodiments, the composition comprising a combination of the Nicotinamide and Vitamin B6 is in the form of a nutritional composition.

In some embodiments, the composition comprising a combination of the Nicotinamide and Vitamin B6 is in the form of a food product, food supplement, nutraceutical, food for special medical purpose (FSMP), nutritional supplement, dairy-based drink, low-volume liquid supplement or meal replacement beverage.

In some embodiments, the composition comprising a combination of the Nicotinamide and Vitamin B6 is in the form of a food additive or a medicament.

A food additive or a medicament may be in the form of tablets, capsules, pastilles or a liquid for example. Food additives or medicaments are preferably provided as sustained release formulations, allowing a constant supply of the active ingredients for prolonged times.

The composition may be selected from the group consisting of milk-powder based products; instant drinks; ready-to-drink formulations; nutritional powders; nutritional liquids; milk-based products, in particular yoghurts or ice cream; cereal products; beverages; water; coffee; cappuccino; malt drinks; chocolate flavoured drinks; culinary products; soups; tablets; and/or syrups.

The composition may further contain protective hydrocolloids (such as gums, proteins, modified starches), binders, film forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and anti-microbials.

Further, the composition may contain an organic or inorganic carrier material suitable for oral or enteral administration as well as vitamins, minerals trace elements and other micronutrients in accordance with the recommendations of government bodies such as the USRDA.

The composition of the invention may contain a protein source, a carbohydrate source and/or a lipid source.

Any suitable dietary protein may be used, for example animal proteins (such as milk proteins, meat proteins and egg proteins); vegetable proteins (such as soy protein, wheat protein, rice protein and pea protein); mixtures of free amino acids; or combinations thereof. Milk proteins such as casein and whey, and soy proteins are particularly preferred.

If the composition includes a fat source, the fat source preferably provides 5% to 40% of the energy of the formula; for example, 20% to 30% of the energy. DHA may be added. A suitable fat profile may be obtained using a blend of canola oil, corn oil and high-oleic acid sunflower oil.

A source of carbohydrates may more preferably provide between 40% to 80% of the energy of the composition. Any suitable carbohydrate may be used, for example sucrose, lactose, glucose, fructose, corn syrup solids, maltodextrins and mixtures thereof.

Another aspect of the present disclosure is a kit comprising a therapeutically effective amount of any of the compositions disclosed herein. In an embodiment, the kit is configured for oral administration of the composition. For example, the kit can be in a form of two capsules, wherein the first capsule comprises the vitamin B6 and the second capsule comprises the Nicotinamide.

Another aspect of the present disclosure is a method of preparing the composition. The method can comprise combining a therapeutically effective amount of a combination of Nicotinamide and vitamin B6, preferably an amount of the combination that is therapeutically effective for at least one of the physiological benefits disclosed herein.

Cachexia and Related Diseases

The invention provides compounds, compositions and methods of preventing and/or treating cachexia or skeletal muscle wasting syndrome by modulating skeletal muscle stem cells. Cachexia is a complex metabolic syndrome associated with underlying illness and characterized by loss of muscle with or without loss of fat mass. The prominent clinical feature of cachexia is weight loss in adults (corrected for fluid retention) or growth failure in children (excluding endocrine disorders).

The invention is especially relevant for cancer precachexia/cachexia. In these conditions, myofiber damages along with an activation of the muscle stem cells have been described. Nevertheless, muscle regeneration fails to properly counteract muscle loss, as muscle stem cell function is impaired displaying a defect in their myogenic commitment. This defect has been proposed as a potential cause of the muscle wasting (He W A, Berardi E, Cardillo V M, Acharyya S, Aulino P, Thomas-Ahner J, Wang J, Bloomston M, Muscarella P, Nau P, Shah N, Butchbach M E, Ladner K, Adamo S, Rudnicki M A, Keller C, Coletti D, Montanaro F, Guttridge D C (2013). NF-κB-mediated Pax7 dysregulation in the muscle microenvironment promotes cancer cachexia. J Clin Invest. November; 123(11):4821-35; Joanna Brzeszczyńska et al., (2016). Loss of oxidative defense and potential blockade of satellite cell maturation in the skeletal muscle of patients with cancer but not in the healthy elderly. Aging. August; 8(8):1690-702).

Cachexia is often seen in patients with diseases such as cancer, chronic heart failure, renal failure, chronic obstructive pulmonary disease, AIDS, autoimmune disorders, chronic inflammatory disorders, cirrhosis of the liver, anorexia, chronic pancreatitis and/or metabolic acidosis and neurodegenerative disease.

There are certain types of cancer wherein cachexia is particularly prevalent, for example, pancreas, esophagus, stomach, bowel, lung and/or liver cancer.

The internationally recognized diagnostic criterion for cachexia is weight loss greater than 5% over a restricted time, for example 6 months, or weight loss greater than 2% in individuals already showing depletion according to current body weight and height (body-mass index [BMI]<20 kg/m²) or skeletal muscle mass (measured by DXA, MRI, CT or bioimpedance). Cachexia can develop progressively through various stages—precachexia to cachexia to refractory cachexia. Severity can be classified according to degree of depletion of energy stores and body protein (BMI) in combination with degree of ongoing weight loss.

In particular, cancer cachexia has been defined as weight loss>5% over past 6 months (in absence of simple starvation); or BMI<20 and any degree of weight loss>2%; or appendicular lean mass consistent with low muscle mass (males<7·26 kg/m²; females<5·45 kg/m²) and any degree of weight loss>2% (Fearon et al. (2011) Definition and classification of cancer cachexia: an international consensus. Lancet Oncology, 12, 489-495).

Precachexia may be defined as weight loss≤5% together with anorexia and metabolic change. At present there are no robust biomarkers to identify those precachectic patients who are likely to progress further or the rate at which they will do so. Refractory cachexia is defined essentially on the basis of the patient's clinical characteristics and circumstances.

It may be appreciated that the compositions and methods of the present invention may be beneficial for the prevention and/or treatment of the condition of precachexia as well as cachexia in particular to promote muscle repair and/or muscle regeneration.

In an embodiment of the invention, the invention provides a method of preventing and/or treating precachexia and/or cachexia, and/or promoting muscle repair, and/or improving skeletal muscle regeneration, and/or maintaining or increasing skeletal muscle function and/or skeletal muscle mass. The method comprises administering to a human or animal subject an effective amount of a composition of the invention.

In an embodiment of the invention, the invention provides a method of treatment of cachexia or precachexia comprising administering to a human or animal subject an effective amount of a composition of the invention wherein cachexia or precachexia is associated with a disease selected from cancer, chronic heart failure, renal failure, chronic obstructive pulmonary disease, AIDS, autoimmune disorders, chronic inflammatory disorders, cirrhosis of the liver, anorexia, chronic pancreatitis, metabolic acidosis and/or neurodegenerative disease.

In a preferred embodiment of the invention, the invention provides a method of treatment of cancer cachexia is associated with cancer is selected from pancreas, esophagus, stomach, bowel, lung and/or liver cancer.

In yet another embodiment of the invention, the invention provides a method of treatment wherein treatment of cancer cachexia is measured by reducing body weight loss, preventing body weight loss, maintaining body weight or increasing body weight.

In another embodiment of the invention, a compound or a composition of the invention may be used in a method of treatment wherein cancer cachexia is a result of treatment for cancer with a chemotherapeutic agent.

Non-limiting examples of the administration include oral administration and intravenous administration. In a preferred embodiment, the administration is oral administration. In an embodiment, the method comprises administering to an individual in need thereof a therapeutically effective amount of a combination of vitamin B6 and Nicotinamide.

In a further embodiment of the invention, a compound or a composition of the invention may be used in a method of prevention or treatment of cachexia or precachexia in combination with a dietary intervention of high caloric, high protein, high carbohydrate, Vitamin B12 and/or Vitamin D supplementation, antioxidants, omega 3 fatty acids, butyrate producers, and/or polyphenols.

Within the context of the present invention, the expression "butyrate producer" indicate a substance or ingredient which, when administered to a subject, is able to deliver and/or stimulate the production of butyrate, for example in the gut of said subject. Not limiting examples of butyrate producers are: sodium butyrate, potassium butyrate and/or triglycerides containing butyrate such as for example those described in the patent application WO 2019/228851 of the same applicant.

In some embodiments, the composition comprising a combination of the Nicotinamide and Vitamin B6 is in a combined preparation for simultaneous, separate or sequential use, preferably simultaneous.

The term "combination", or terms "in combination", "used in combination with" or "combined preparation" as used herein may refer to the combined administration of two or more agents simultaneously, sequentially or separately.

The term "simultaneous" as used herein means that the agents are administered concurrently, i.e. at the same time.

The term "sequential" as used herein means that the agents are administered one after the other.

The term "separate" as used herein means that the agents are administered independently of each other but within a time interval that allows the agents to show a combined, preferably synergistic, effect. Thus, administration "separately" may permit one agent to be administered, for example, within 1 minute, 5 minutes or 10 minutes after the other.

The skilled person can readily determine an appropriate dose of one of the agents of the invention to administer to a subject without undue experimentation. Typically, a physician will determine the actual dosage which will be most suitable for an individual patient and it will depend on a variety of factors including the activity of the specific agent employed, the metabolic stability and length of action of that agent, the age, body weight, general health, sex, diet, mode and time of administration, rate of excretion, drug combination, the severity of the particular condition, and the individual undergoing therapy. There can of course be individual instances where higher or lower dosage ranges are merited, and such are within the scope of the invention.

In an embodiment, the method comprises administering to an individual in need thereof a therapeutically effective amount of a combination of vitamin B6 in an amount of 1.0-12.0 mg of the vitamin B6/300 Kcal energy and/or a daily dosage of 1.0-25.0 mg of the vitamin B6/day and Nicotinamide in an amount of about 0.001 mg/day to about 2000 mg/day, preferably about 0.001 mg/day to about 1000 mg/day.

In an embodiment, the combination is administered to the individual for a time period of at least one month; preferably at least two months, more preferably at least three, four, five or six months; most preferably for at least one year. During the time period, the combination can be administered to the individual at least one day per week; preferably at least two days per week, more preferably at least three, four, five or six days per week; most preferably seven days per week. The combination can be administered in a single dose per day or in multiple separate doses per day.

The above examples of administration do not require continuous daily administration with no interruptions. Instead, there may be some short breaks in the administration, such as a break of two to four days during the period of administration. The ideal duration of the administration of the composition can be determined by those of skill in the art.

Subject

In some embodiments, a subject is a human or non-human animal.

Examples of non-human animals include vertebrates, for example mammals, such as non-human primates (particularly higher primates), dogs, rodents (e.g. mice, rats or guinea pigs), pigs and cats. The non-human animal may be a companion animal.

Preferably, the subject is a human.

EXAMPLES

The following non-limiting examples support the unexpected effectiveness of a composition comprising Nicotinamide and Vitamin B6 for promoting or improving muscle repair, skeletal muscle regeneration, muscle function and/or muscle mass.

Example 1—Myogenic Amplification and Commitment of Muscle Stem Cells

Material and Methods

Human primary myoblasts from different donors (donor 1, donor 2 or donor 3) were seeded in 384 well plates at a density of 1'000 cells per well in skeletal muscle growth medium (SKM-M, AMSbio). For treatment, compounds were directly added to the myoblast cultures 16 hours after initial plating.

All cultures were then grown for 96 hours. Cells were stained for Pax7 and MyoD expression using antibodies directed against Pax7 and MyoD and counterstained with Hoechst 33342 to visualize cell nuclei. Pax7+ cells are defined as cells that express Pax7 regardless of MyoD expression. MyoD+ cells are defined as cells that do not express Pax7 but express MyoD. Image acquisition was performed using the ImageXpress (Molecular Devices) platform. Custom module analysis based on Multi-Wavelength Cell Scoring of the MetaXpress software was used for quantification. Additionally, several ratios between Pyridoxine and Nicotinamide (ratio B6/NAM) ranging from 1:2 to 1:80 were tested, and FIG. 5 represents the number of Pax7+ cells for these specific ratios. Data are expressed as number of cells per arear of injured muscle.

*, , *, **** indicates difference from the control, One-way ANOVA, with $p<0.05$, $p<0.01$, $p<0.001$, $p<0.0001$, respectively. Data are presented as Mean+/−SEM Results Results are presented in FIGS. 1 to 5.

Data obtained from Human primary myoblasts from donors 1 and 2 were pooled (see FIG. 1). For each condition, the total number of cells was determined to evaluate compound toxicity, and the number of Pax7+ or MyoD+ cells was normalized to the total cell number in order to evaluate the proportion of this population and expressed as a fold change compared to the control condition (DMSO 1%). FIG. 1A represents the proportion of Pax7+ cells and FIG. 1B represents the proportion of MyoD+ cells. These data demonstrate that Nicotinamide promotes Muscle Stem Cell function by increasing the proportion of both amplifying (Pax7+) and differentiating (MyoD+) cells in a dose dependent manner.

Similarly for Pyridoxine, data obtained from Human primary myoblasts from donors 1 and 2 were pooled. For each condition, the total number of cells was determined to evaluate compound toxicity, and the number of Pax7+ or MyoD+ cells was normalized to the total cell number in order to evaluate the proportion of this population and expressed as a fold change compared to the control condition (DMSO 1%). FIG. 2A represents the proportion of Pax7+ cells and FIG. 2B represents the proportion of MyoD+ cells. These data demonstrate that Pyridoxine promotes Muscle Stem Cell function by increasing the proportion of differentiating (MyoD+) cells in a dose dependent manner.

FIG. 3 represents the effect of nicotinamide and pyridoxine alone or combined on MyoD+ cells (from donor 3). For each condition, the number of MyoD+ cells was normalized to the number of MyoD+ cells in the control condition (DMSO 1%). FIG. 3A represents the number of MyoD+ cells normalized to the control condition. FIG. 3B represents the increase in MyoD+ cell number compared to the control condition (DMSO 1%). These data show that the effect of the combination of Nicotinamide and Pyridoxine is greater than the sum of the individual effect of Nicotinamide and Pyridoxine, indicating a synergistic effect. Indeed, by applying a linear regression model (interaction term, $p=0.05$), we were able to observe a statistically significant synergistic effect between the nicotinamide and pyridoxine.

As a comparative result, Combination of Nicotinamide (NAM) with vitamin B9 was measured similarly as above (see FIG. 4). Unlike pyridoxine (vitamin B6), vitamin B9, another member of the B vitamin complex, does not have any addictive nor synergistic effect when added in combination with Nicotinamide. Additionally, FIG. 5 demonstrates that the ratio between Pyridoxine and Nicotinamide (ratio Vitamin B6/NAM) has a relevant impact on promoting muscle stem cell function.

Example 2 In Vivo Effect of the Combination of Nicotinamide (NAM) and Pyridoxine (B6) on Muscle Stem Cells Function

Material and methods

In order to mimic the physiological process of muscle regeneration that occurs in skeletal muscles in response to injury or disease, we performed an intramuscular injection of cardiotoxin into mouse hindlimb muscles. One week prior to the induction of the muscle injury, mice were given by oral gavage Nicotinamide and pyridoxine (at 200 and 4 mg/kg body weight, respectively) vs. water control. Mice were treated once a day until the end of the experiment. To evaluate the muscle stem cell activity and the efficiency of the muscle regeneration, muscles that have been previously injured were harvested 5 days after the injury and cryosections were prepared. Cryosections were stained for Pax7 and Myogenin using specific antibodies and counterstained with Hoechst 33342 to visualize cell nuclei. Early phase of expansion and subsequent phase of myogenic differentiation of Muscle Stem Cells were evaluated by counting the number of Pax7+ cells (FIG. 6A) and myogenin+ cells (FIG. 6B), respectively.

\*, \*\*, \*\*\*, \*\*\*\* indicates difference from the control, One-way ANOVA, with $p<0.05$, $p<0.01$, $p<0.001$, $p<0.0001$, respectively. Data are presented as Mean+/−SEM.

Results

These data demonstrate that a combination of Nicotinamide and Pyridoxine promotes Muscle Stem Cell function by increasing the number of both amplifying (Pax7+) and differentiating (MyoD+) cells in an in vivo preclinical model of muscle repair/regeneration (FIG. 6).

Example 3: Safety of Compounds as Non-Oncogenic

Material and methods

The safety of the compounds were tested in two different human cancer cell lines purchased from ATCC. Serum and FGF (Fibroblast Growth Factor) conditions were used as positive controls. \*, \*\*, \*\*\*, \*\*\*\* indicates difference from the control, One-way ANOVA, with $p<0.05$, $p<0.01$, $p<0.001$, $p<0.0001$, respectively. Data are presented as Mean+/−SEM.

Cell line PC-3 of prostate/adenocarcinoma from a Caucasian male, aged 62 years (FIG. 7A)

Cell line PANC-1 was from a pancreatic duct epitheloid carcinoma from a Caucasian male, aged 56 years (FIG. 7B).

Results

The data shown in FIG. 7 demonstrate that Nicotinamide and pyridoxine whether alone or used in combination have no effect on the proliferation of cancer cells.

Various changes and modifications to the presently preferred embodiments disclosed herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method for treating cachexia or precachexia, promoting skeletal muscle regeneration, and/or promoting skeletal muscle repair, and/or for improving skeletal muscle mass, skeletal muscle strength and/or skeletal muscle function in an individual with cachexia or precachexia, the method comprising administering to the individual a therapeutically effective amount of a composition comprising a combination of vitamin B6 and Nicotinamide in a weight ratio of from about 1:100 to about 1:30.

2. The method according to claim 1, wherein the vitamin B6 is administered in an amount of about 1.0-600 mg vitamin B6 per day.

3. The method according to claim 1, wherein the Nicotinamide is administered in an amount of about 1 mg/day to about 3000 mg/day.

4. The method according to claim 1, wherein the Vitamin B6 is administered in an amount of 10-20.0 mg vitamin B6 per day, and the Nicotinamide is administered in an amount of about 500 mg to about 1000 mg Nicotinamide per day.

5. The method according to claim 1, wherein the vitamin B6: Nicotinamide are present in a ratio of from about 1:60 to about 1:30.

6. The method according to claim 1, wherein the composition is in a form selected from the group consisting of an oral nutritional composition, a nutritional supplement, an oral nutritional supplement, a medical food, a food supplement, a food product, and a food for special medical purpose (FSMP).

7. The method according to claim 1, wherein the composition is in a form selected from the group consisting of a solid powder, a powdered stick, a capsule and a liquid.

8. The method according to claim 1, wherein the administering of the therapeutically effective amount of the composition treats the precachexia or cachexia in the individual.

9. The method according to claim 1, wherein the cachexia or precachexia is associated with a disease selected from the group consisting of cancer, chronic heart failure, renal failure, chronic obstructive pulmonary disease, AIDS, autoimmune disorders, chronic inflammatory disorders, cirrhosis of the liver, anorexia, chronic pancreatitis, metabolic acidosis, neurodegenerative disease, and combinations thereof.

10. The method according to claim 1, wherein the cachexia or precachexia is associated with at least one cancer selected from the group consisting of pancreas, esophagus, stomach, bowel, bladder, lung and liver cancer.

11. The method according to claim 1, wherein the cachexia is a result of treatment for cancer with a chemotherapeutic agent.

12. The method according to claim 1, wherein the composition further comprises a component selected from the group consisting of protein, carbohydrate, fat and mixtures thereof.

13. The method according to claim 1, wherein the administering of the therapeutically effective amount of the composition promotes skeletal muscle regeneration and/or promotes skeletal muscle repair in the individual.

14. The method according to claim 1, wherein the administering of the therapeutically effective amount of the composition improves skeletal muscle mass, skeletal muscle strength and/or skeletal muscle function in the individual.

\* \* \* \* \*